United States Patent
Shieh

(10) Patent No.: US 9,592,205 B2
(45) Date of Patent: Mar. 14, 2017

(54) FASCILE SYNTHESIS OF BIOCOMPATIBLE POLYMER CAPSULE NANOPARTICLES FOR DRUG ENCAPSULATION

(71) Applicant: Dar-Bin Shieh, Tainan (TW)

(72) Inventor: Dar-Bin Shieh, Tainan (TW)

(73) Assignee: NATIONAL CHENG KUNG UNIVERSITY (TW)

(*) Notice: Subject to any disclaimer, the term of this patent is extended or adjusted under 35 U.S.C. 154(b) by 996 days.

(21) Appl. No.: 13/624,038

(22) Filed: Sep. 21, 2012

(65) Prior Publication Data

US 2013/0071472 A1    Mar. 21, 2013

Related U.S. Application Data

(60) Provisional application No. 61/537,152, filed on Sep. 21, 2011.

(51) Int. Cl.
| | |
|---|---|
| *A61K 9/50* | (2006.01) |
| *A61K 9/51* | (2006.01) |
| *A61K 31/337* | (2006.01) |
| *B82Y 5/00* | (2011.01) |

(52) U.S. Cl.
CPC .......... *A61K 9/5192* (2013.01); *A61K 9/5153* (2013.01); *A61K 31/337* (2013.01); *B82Y 5/00* (2013.01); *Y10S 977/788* (2013.01); *Y10S 977/915* (2013.01)

(58) Field of Classification Search
CPC ........ A61K 9/50; A61K 9/501; A61K 9/5015; A61K 9/5031; A61K 9/5036; A61K 9/51; A61K 9/5107; A61K 9/5115; A61K 9/5146; A61K 9/5153; A61K 9/5192

USPC .................................................. 424/464–489
See application file for complete search history.

(56) References Cited

U.S. PATENT DOCUMENTS

| | | | |
|---|---|---|---|
| 4,608,278 A * | 8/1986 | Frank ................... | A61K 9/5026 252/363.5 |
| 5,543,158 A | 8/1996 | Gref et al. | |
| 2005/0250881 A1 * | 11/2005 | Gref ..................... | A61K 9/5161 523/440 |
| 2006/0141025 A1 | 6/2006 | Huang et al. | |
| 2009/0246123 A1 * | 10/2009 | Zanella ................. | A61K 47/10 424/1.11 |
| 2010/0173000 A1 | 7/2010 | Libin et al. | |
| 2010/0196280 A1 * | 8/2010 | Fischer ................ | A61K 9/5138 424/9.3 |

FOREIGN PATENT DOCUMENTS

WO    2009046446 A2    4/2009

* cited by examiner

*Primary Examiner* — Micah-Paul Young
(74) *Attorney, Agent, or Firm* — Bacon & Thomas, PLLC

(57) ABSTRACT

The present invention relates to a method for preparing a capsule nanoparticle used in encapsulating hydrophobic medicines, comprising the following steps: (A) providing a biocompatible polymer and an organic solution containing a hydrophobic medicine; (B) stirring the organic solution at 3-10° C., and titrating with an alcohol solution, so as to make the biocompatible polymer encapsulate hydrophobic medicine to form a capsule nanoparticle; (C) ultrasonic vibrating the capsule nanoparticle at 3-10° C.; (D) filtering the capsule nanoparticle to an average size controllable in the range of 60-450 nm; and (E) lyophilizing the encapsulated particles.

13 Claims, 2 Drawing Sheets

FASCILE SYNTHESIS OF BIOCOMPATIBLE POLYMER CAPSULE NANOPARTICLES FOR DRUG ENCAPSULATION

CROSS REFERENCE TO RELATED APPLICATION

This application claims the benefit of filing date of U.S. Provisional Application Ser. No. 61/537,152, entitled "Fascile Synthesis of Biocompatible Polymer Nanoencapsules for Drug Encapsulation" filed Sep. 21, 2011 under 35 USC §119(e)(1).

BACKGROUND OF THE INVENTION

1. Field of the Invention

The present invention relates to a method for preparing a capsule nanoparticle used in encapsulating hydrophobic medicines, and more particularly, to a method which may rely on hypothermic vibration to form a stable capsule nanoparticle used in encapsulating hydrophobic medicines.

2. Description of Related Art

Development demand for portable medicinal system continues to expand as trend in pharmaceutical development grows at an increasing rate. The current state of research focusing on carriers for encapsulating or carrying medicine are mainly oriented towards solving the physical or chemical properties of the surface of medicine, so as to make itself more compatible with biomaterials, and promote medical treatment for focused ailment.

It will be understood by a person having ordinary skill in the art that hydrophobic medicines can operate to encapsulate medicines through gel phase separation method, emulsification, redox, and other physical or chemical methods, so as to enhance maintaining efficacy of the medicine, lengthen the period of pharmaceutical effect and better secure the purpose of delivering medicine to the target cells.

There may be a variety of biocompatible materials for use in encapsulating hydrophobic medicines, such as poly-(D, L-lactide-co-glycolide), liposome and others, the major technique for which is to promote encapsulation of hydrophobic medicines by addition of surfactants, and ultimately screen out appropriate medicine size by to encapsulate particles by use of filtration. However in reality, for medicines having temperature sensitivity, encapsulation process under room temperature can likely undermine the pharmaceutical efficacy of the medicine, and the surfactant used in encapsulation process can likely produce toxicity if not itself completely removed, or can react with medicine to produce undesired pharmaceutical effect.

In consideration of the above, there is an urgent need to develop a medicine encapsulation technique to resolve a problem in encapsulating hydrophobic medicines, which extends to cover encapsulating medicine while not destroying pharmaceutical efficacy, while also facilitating maintaining pharmaceutical efficacy by mass automation production of medicine encapsulation.

SUMMARY OF THE INVENTION

A major object of the present invention is to provide a method for preparing a capsule nanoparticle used in encapsulating hydrophobic medicines, so as to prepare stable and convenient for storage capsule nanoparticle encapsulating hydrophobic medicines.

In order to achieve the abovementioend object, the present invention provides a method for preparing capsule nanoparticle for use in encapsulating hydrophobic medicine, comprising the steps of: (A) providing an organic solution having a biocompatible polymer and a hydrophobic medicine; (B) stirring the organic solution at a low temperature of 3 to 10° C., and titrating with a alcohol solution, to make the biocompatible polymer encapsulate the hydrophobic medicine to form a capsule nanoparticle; (C) ultrasonic vibrating the capsule nanoparticle at a low temperature of 3 to 10° C.; (D) filtering the capsule nanoparticle, to make an average capsule nanoparticle diameter of the capsule nanoparticle at 60-450 nm; and (E) lyophilizing the capsule nanoparticle, so as to attain the purpose of long-term storage.

In the abovementioned process, the biocompatible polymer can be a material approved by the U.S. Food and Drug Administration, it is not particularly limited, and is preferably selected from the group consisting of: poly-(D,L-lactide-co-glycolide), PLA, and PEG-PLA, but is more preferably poly-(D,L-lactide-co-glycolide). Also, the abovementioned hydrophobic medicine is appropriate as long as it has a hydrophobic property, and is more preferred to be an anti-cancer medicine having hydrophobic property or small molecule inhibitor, but is much preferred to be a hydrophobic medicine at least selected from a group consisting of phyxol, J-3-, LY 294002 and AG490. Furthermore, the abovementioned organic solution is not particularly limited, and is more preferred to be a ketone solution, and much preferred to be an acetone solution.

The alcohol titrating solution in step (B) of the present invention is not particularly limited, but more preferred to be ethanol solution. In addition, in the abovementioned process, it is more preferred to stir at a low temperature of 4-6° C., and carry out alcohol solution based titration. Furthermore, in the present titration process, it is required to keep the desired titrating solution at a low stirring speed, which is more preferred to be 3-10 rpm, but much preferred to be 5-6 rpm. Here, low temperature stirring is adopted so as to stabilize the pharmaceutical efficacy of the hydrophobic medicine, to avoid pharmaceutical efficacy deterioration as resulting from metamorphism during encapsulation process.

In step (C) of the present invention, it is preferred to carry out the ultrasonic vibration on capsule nanoparticles of step (B) at 4-6° C. Through low temperature ultrasonic vibration, it is on the one hand possible to prevent hydrophobic medicine from undertaking metamorphism, and also on the other hand to lower and homogenize particle diameter of capsule nanoparticles.

In step (D) of the present invention, the average size particle of the capsule nanoparticle is more preferred to be between 90-350 nm, and much preferred to be between 100-200 nm, or much preferred to be between 150-250 nm.

Step (C) of the present invention can further comprise a step (C1): adding the organic solution having the capsule nanoparticle into a milli Q water (M.Q water), and ultrasonic vibrating the capsule nanoparticle; in addition to this, step (C) can further comprise a step (C2): eliminating the organic solution in the milli Q water. Here, method for eliminating organic solution in the millie Q water having capsule nanoparticle is not particularly limited, which can be eliminated by, for example, volatization, dialysis, dilution, and other methods. It is more preferred to eliminate organic solution in the millie Q water having capsule nanoparticle by dialysis.

Furthermore, step (E) of the abovementioned invention further comprises a step (E1): replacing the millie Q water having the capsule nanoparticle with a millie Q water having sucrose and the capsule nanoparticle, so as to form isotonic solution in addition to being used as an excipient.

For capsule nanoparticle encapsulating hydrophobic medicine that is prepared by the method of the present invention as described above, the encapsulation rate can be computed by Formula 1 cited below, which can be between 10-90%, more preferred to be between 30-80%, and much preferred to be between 40-60%.

Encapsulation Rate (%)=Amount of Medicine
Encapsulated in the Biocompatible Polymer/
Total Amount of Medicine            [Formula 1]

The present invention is mainly directed to achieving encapsulation of hydrophobic medicine and alteration of surface property of the hydrophobic medicine by way of automatic production in conjunction with ultrasonic vibration under a low temperature environment and a condition not requiring use of surfactant. Examples of surface property therein include hydrophilic property and others. Method of the present invention can increase encapsulation rate of the hydrophobic medicine (based on the known art of 20% encapsulation rate going upward to approximately 50% encapsulation rate), to encapsulate hydrophobic medicine through biocompatible polymer (such as PLGA). By the method of the present invention provided here, the encapsulated hydrophobic medicine can have the property of pharmacokinetic improvement, including increasing residence time in the blood, and prolonging effect period of the tumor treatment agent, while also improving anti-medicine problem of the tumor against medicine, so as to enhance the treatment effect of the medicine with minimum complication by side effects. In addition, one benefit of carrying out encapsulation process using ultrasonic vibration is that it can not only ensure the medicine's upholding to its medicinal effect, but also form hydrophobic-medicine-encapsulating capsule nanoparticles having homogenized particle diameter, and even more achieve effect of long-term isothermal storage. Suitable isotonic solution (such as saline water) can be turned to for redissolving as required, and such can also achieve an expected effect.

DETAILED DESCRIPTION OF THE PREFERRED EMBODIMENT

The invention is capable of other embodiments and of being practiced or carried out in various ways. Variations and modifications of the foregoing are within the scope of the present invention. It will also be understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

Embodiment 1—Preparation of PLGA Capsule Nanoparticles Encapsulating Phyxol Hydrophobic Medicines The present embodiment of the current invention uses poly-(D,L-lactide-co-glycolide) biocompatible polymers to encapsulate phyxol hydrophobic medicines to present an exemplary capsule nanoparticle embodiment.

Dissolve 2.5 g PLGA (lactide:glycolide=50:50, 4.5 A, M.W.=66 kDA) and 50 mg phyxol (pacilitaxel) in 250 mL organic acid added acetone solution, rotate the solution at 200-3000 rpm, and stir at 4° C. for 5-30 minutes, to thereby form a transparent PLGA/phyxol/acetone mixture solution. Then lower the stirring rotation down to 5 rpm, and titrate the 50% ethanol (24 μl/drop) with a vibrational pump to the abovementioned mixture solution. Meanwhile, subject the form-developing PLGA capsules to vibration using ultrasonic vibration (maximum instant power=2000 W), to decrease the diameter of the capsule nanoparticle. Continue titrating ethanol to the mixture solution to turn from transparent to semi-transparent before stopping titration process and proceeding with hypothermic ultrasonic vibration for 15 minutes. Subsequently, rapidly inject with syringe (23 G needle) semi-transparent mixture solution into 1 L sterile milli Q water (M.Q. water) to form white gel-like solution, then, maintain the white gel-like solution at 4° C. under a ultrasonic vibration environment for 30 minutes, to stabilize the structure of the PLGA capsule nanoparticle encapsulating phyxol. Next, eliminate acetone solution from the white gel-like solution by volatization.

Figure 1:
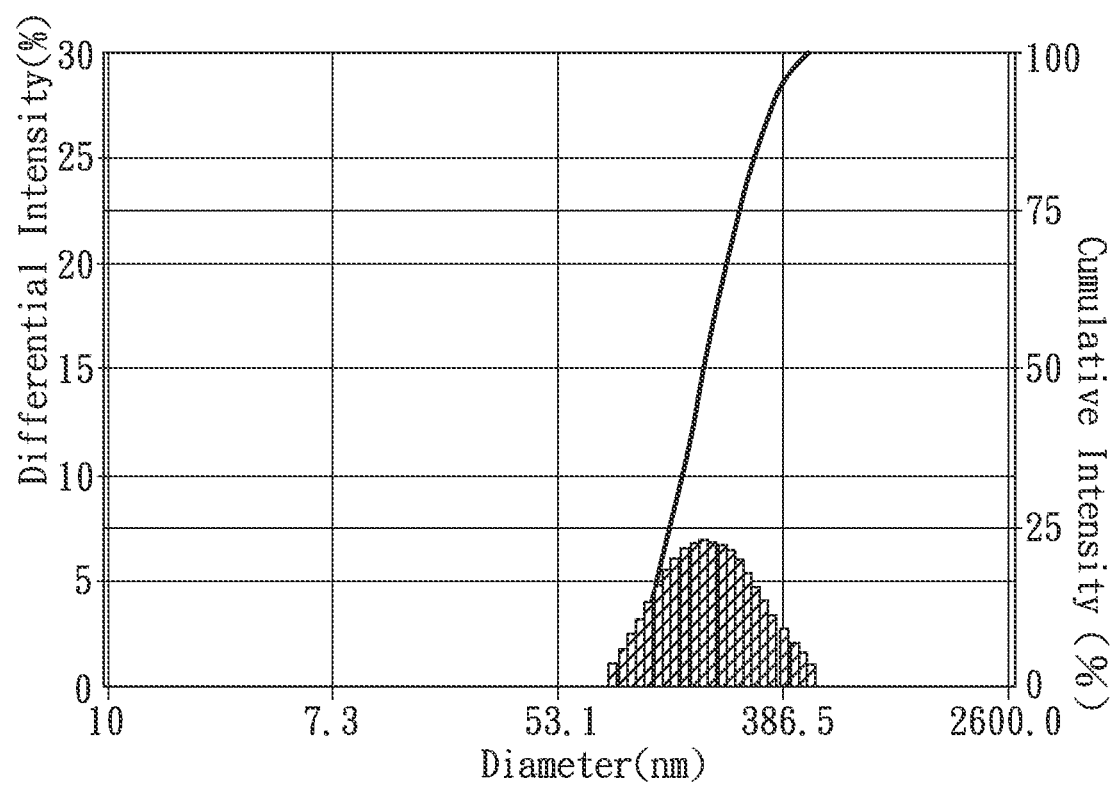
FIG. 1 shows a capsule nanoparticle size diameter distribution graph according to embodiment 1 of the present invention.

After filtering the aggregated capsules out of the abovementioned white gel-like products by the use of a filter having 40 μm hole diameter, measure the capsule nanoparticle size. The result is as shown in FIG. 1, the capsule nanoparticle diameter measurement result contains a peak amplitude, having a standard deviation of 90.1, average capsule nanoparticle diameter distribution of 217.7 nm, and the capsule nanoparticle has a negatively charged surface charge.

In order to eliminate PLGA that does not encapsulate hydrophobic medicines, phyxol that is not itself encapsulated, and organic acid in the mixture solution, carry out diafiltration of diafiltration of TFF system (tangential flow filtration) in order to remove materials having a size smaller than 100 nm. After the diafiltration is done, the capsule nanoparticle size of the PLGA capsule nanoparticle encapsulating phyxol is approximately 170 nm. An observation by use of a transparent electronic microscopy (TEM) for capsule nanoparticle's shape reveals an irregular, oval shape.

In consideration for further stabilizing phyxol hydrophobic medicines encapsulated in PLGA, dissolve diafiltrated white gel-like solution in a 5% sucrose solution before carrying out lyophilizing, then maintain lyophilizing for two days in order to form powder-shaped solids. The powder-shaped solids may be re-dissolved in milli Q water (M.Q. water) or isotonic solution for use, before as desired.

Embodiment 2—Measurement for the In Vitro Efficacy of Capsules of Embodiment 1

Figure 2:
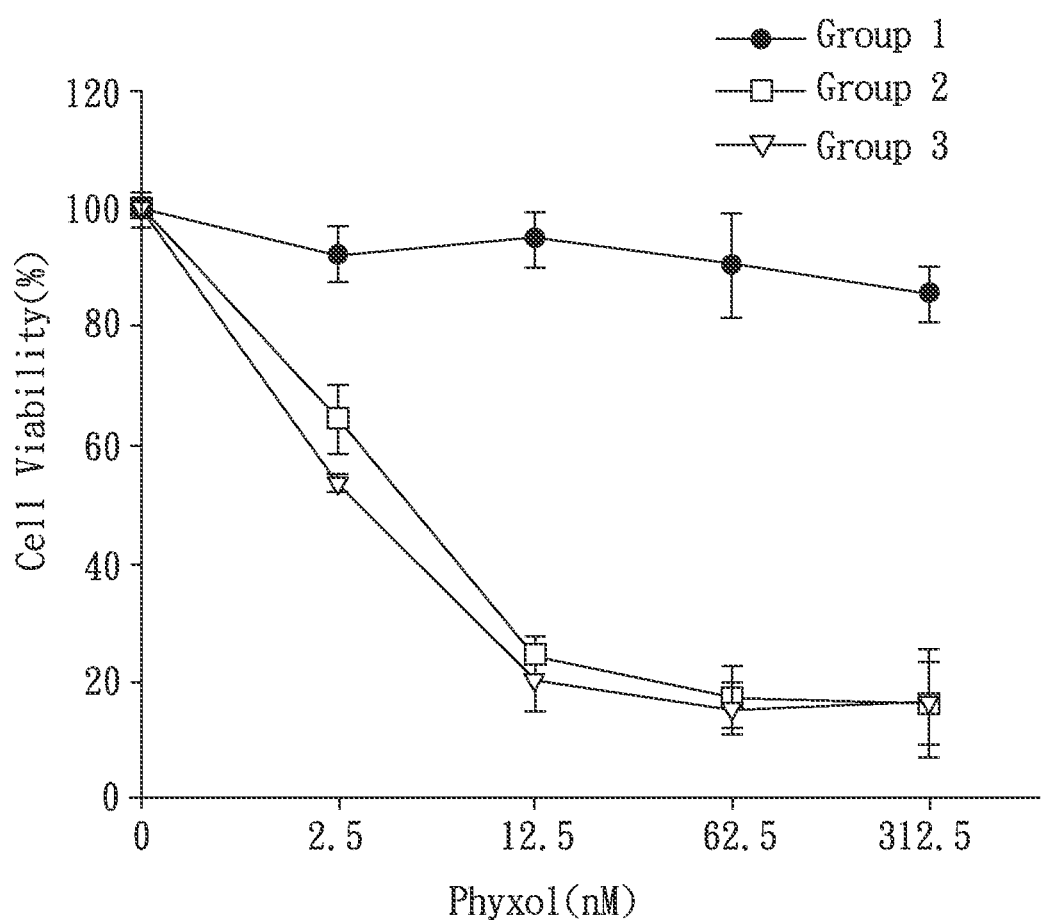
FIG. 2 shows an experimental result demonstrating in-vitro pharmaceutical efficacy.

Re-dissolve the capsule nanoparticle from embodiment 1, and measure the in-vitro pharmaceutical efficacy using AS-2 lung cancer model, the result is as shown in FIG. 2.

This embodiment of the present invention adds samples of different conditions after the AS-2 lung cancer cell is cultured for 48 hours in order to observe cell viability. The present embodiment's experiment is assigned into three groups, in which the first group merely adds PLGA samples; the second group adds phyxol samples not subject to encapsulation; the third group adds capsules having phyxol, and the added sample concentration of the three experiments are all 0 nM, 2.5 nM, 12.5 nM, 62.5 nM and 312.5 nM. It will be clearly observed from the results shown in FIG. 2 that cell viability for group 1 almost stays undisturbed, the cell viability for group 2 and group 3 clearly decrease from 100% to less than 20%, this result demonstrates that in addition to the method of the present invention being not prone to making the pharmaceutical efficacy of encapsulated medicine inferior, the capsules prepared by the method of the present invention (which is the capsule nanoparticle from embodiment 1), almost have the same pharmaceutical efficacy as the naked medicine, and are almost identical to the pharmaceutical efficacy of non-encapsulated phyxol (group 2).

The foregoing describes the invention including preferred forms thereof. Alterations and modifications as will be obvious to those skilled in the art are intended to be incorporated within the scope of the invention as defined in the accompanying claims.

What is claimed is:

1. A method for preparing capsules encapsulating hydrophobic medicines, comprising the steps of:
   (A) providing an organic solution having a biocompatible polymer and a hydrophobic medicine;
   (B) stirring the organic solution at a low temperature of 3 to 10° C., and titrating with an alcohol solution, to make the biocompatible polymer encapsulate the hydrophobic medicine to form a capsule nanoparticle;
   (C) ultrasonic vibrating the capsule nanoparticle at a low temperature of 3 to 10° C.;
   (D) filtering the capsule nanoparticle, to make an average capsule nanoparticle diameter of the capsule nanoparticle at 60-450 nm; and
   (E) lyophilizing the capsule nanoparticle;
   Wherein the biocompatible polymer is selected from the group consisting (poly-(D,L-lactide-co-glycolide)), PLA, and PEG-PLA;
   and wherein the steps (A) to (E) are performed without surfactant.

2. The method for preparing capsules encapsulating hydrophobic medicines according to claim 1, wherein the hydrophobic medicine is an anti-cancer medicine.

3. The method for preparing capsules encapsulating hydrophobic medicines according to claim 2, wherein, the anti-cancer is at least selected from the group consisting of: phyxol, J-30, LY 294002 and AG490.

4. The method for preparing capsules encapsulating hydrophobic medicines according to claim 1, wherein the organic solution is acetone solution.

5. The method for preparing capsules encapsulating hydrophobic medicines according to claim 1, wherein, step (B) is stirring the organic solution at a low temperature of 4-6° C.

6. The method for preparing capsules encapsulating hydrophobic medicines according to claim 1, wherein the alcohol is an ethanol solution.

7. The method for preparing capsules encapsulating hydrophobic medicines according to claim 1, wherein step (C) is ultrasonic vibrating the capsule nanoparticle at a low temperature of 4-6° C.

8. The method for preparing capsules encapsulating hydrophobic medicines according to claim 1, wherein step (C) further comprises a step (C1):
   (C1) adding the organic solution having the capsule nanoparticle into a milli Q water (M.Q water), and ultrasonic vibrating the capsule nanoparticle.

9. The method for preparing capsules encapsulating hydrophobic medicines according to claim 8, wherein step (C) further comprises a step (C2):
   (C2) eliminating the organic solution in the milli Q water.

10. The method for preparing capsules encapsulating hydrophobic medicines according to claim 9, wherein in step (C2), remaining organic solution in the milli Q water is eliminated through dialysis.

11. The method for preparing capsules encapsulating hydrophobic medicines according to claim 1, wherein, an average capsule nanoparticle diameter of the capsule nanoparticle is 150-250 nm.

12. The method for preparing capsules encapsulating hydrophobic medicines according to claim 9, step (E) further comprises a step (E1):
   (E1) replacing the milli Q water having the capsule nanoparticle with a milli Q water having sucrose and the capsule nanoparticle.

13. The method for preparing capsules encapsulating hydrophobic medicines according to claim 1, wherein, an encapsulation rate for the biocompatible polymer encapsulating the hydrophobic medicine is 10-90%.

* * * * *